US00PP17900P2

(12) United States Plant Patent
Schräder

(10) Patent No.: US PP17,900 P2
(45) Date of Patent: Aug. 7, 2007

(54) ***BIDENS* PLANT NAMED 'SUMBID 03'**

(50) Latin Name: *Bidens ferulifolia*
Varietal Denomination: Sumbid 03

(76) Inventor: Ralf Schräder, Karl-Leisner-Str. 15, D-59348 Lüdinghausen (DE)

( * ) Notice: Subject to any disclaimer, the term of this patent is extended or adjusted under 35 U.S.C. 154(b) by 0 days.

(21) Appl. No.: 11/323,425

(22) Filed: Dec. 30, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

PUBLICATIONS

GTITM UPOVROM Citation for 'SUMBID 03' as per QZ PBR 20041458; Jul. 30, 2004.*

* cited by examiner

*Primary Examiner*—Kent Bell
(74) *Attorney, Agent, or Firm*—C. A. Whealy

(57) ABSTRACT

A new and distinct cultivar of *Bidens* plant named 'Sumbid 03', characterized by its outwardly spreading to cascading plant habit; freely branching habit; dense and bushy appearance; large inflorescences with seven to eight bright yellow-colored ray florets; and freely flowering habit.

1 Drawing Sheet

Botanical designation: *Bidens ferulifolia.*
Cultivar denomination: 'Sumbid 03'.

BACKGROUND OF THE INVENTION

The present Invention relates to a new and distinct cultivar of *Bidens* plant, botanically known as *Bidens ferulifolia* and referred to by the name 'Sumbid 03'.

The new *Bidens* is a product of a planned breeding program conducted by the Inventor in Straβwalchen, Austria. The objective of the breeding program was to create new vigorous *Bidens* cultivars with attractive foliage and large flowers.

The new *Bidens* originated from a cross-pollination made by the Inventor in April, 2002 of the *Bidens ferulifolia* cultivar Sumbid 01, not patented, as the female, or seed, parent with the *Bidens ferulifolia* cultivar Goldmarie, not patented, as the male, or pollen, parent. The cultivar Sumbid 03 was discovered and selected by the Inventor as a flowering plant within the progeny of the stated cross-pollination in a controlled environment in Straβwalchen, Austria in August, 2002.

Asexual propagation of the new cultivar by terminal cuttings at Straβwalchen, Austria since November, 2002, has shown that the unique features of this new *Bidens* are stable and reproduced true to type in successive generations.

SUMMARY OF THE INVENTION

The cultivar Sumbid 03 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sumbid 03'. These characteristics in combination distinguish 'Sumbid 03' as a new and distinct cultivar of *Bidens:*

1. Outwardly spreading to cascading plant habit.
2. Freely branching habit; dense and bushy appearance.

3. Large inflorescences with seven to eight bright yellow-colored ray florets.
4. Freely flowering habit.

Compared to plants of the female parent, the cultivar Sumbid 01, plants of the new *Bidens* had larger inflorescences and more ray florets per inflorescence. Compared to plants of the male parent, the cultivar Goldmarie, plants of the new *Bidens* are more compact and more cascading than plants of the cultivar Goldmarie.

The new *Bidens* can be compared to plants of the *Bidens* cultivar Bidantis, disclosed in U.S. Plant Pat. No. 15,220. However, in side-by-side comparisons, plants of the new *Bidens* differed from plants of the cultivar Bidantis in the following characteristics:

1. Plants of the new *Bidens* were more compact than plants of the cultivar Bidantis.
2. Plants of the new *Bidens* were more cascading than and not as upright as plants of the cultivar Bidantis.
3. Plants of the new *Bidens* were denser and bushier than plants of the cultivar Bidantis.
4. Plants of the new *Bidens* had smaller leaves than plants of the cultivar Bidantis.
5. Plants of the new *Bidens* were more freely flowering than plants of the cultivar Bidantis.
6. Plants of the new *Bidens* had larger inflorescences than plants of the cultivar Bidantis.
7. Inflorescences of plants of the new *Bidens* had more ray florets than inflorescences of plants of the cultivar Bidantis.

BRIEF DESCRIPTION OF THE PHOTOGRAPH

The accompanying colored photograph illustrates the overall appearance of the new *Bidens,* showing the colors as true as it is reasonably possible to obtain in colored reproductions of this type. Colors in the photograph may differ slightly from the color values cited in the detailed botanical description which accurately describe the actual colors of the new *Bidens*. The photograph comprises a side perspective view of a typical flowering plant of 'Sumbid 03' grown in a container.

DETAILED BOTANICAL DESCRIPTION

The following observations, measurements and values describe 37-cm containers with five plants of the new cultivar grown in Lüdinghausen, Germany during the spring and summer and under outdoor, full-sun conditions with day temperatures ranging from 16° C. to 30° C. and night temperatures ranging from 8° C. to 14° C. Plants used for the description were about four months old when the photographs and the description were taken. Color references are made to The Royal Horticultural Society Colour Chart, 2001 Edition, except where general terms of ordinary dictionary significance are used.

Botanical classification: *Bidens ferulifolia* cultivar Sumbid 03.

Parentage:

*Female, or seed, parent.*—*Bidens ferulifolia* cultivar Sumbid 01, not patented.

*Male, or pollen, parent.*—*Bidens ferulifolia* cultivar Goldmarie, not patented.

Propagation:

*Type.*—By terminal cuttings.

*Time to initiate roots, summer.*—About 14 days at 16° C.

*Time to initiate roots, winter.*—About 18 days at 16° C.

*Time to develop roots, summer.*—About 24 days at 16° C.

*Time to develop roots, winter.*—About 28 days at 16° C.

*Root description.*—Fibrous, fine; color, 162C.

*Rooting habit.*—Freely branching; moderately dense.

Plant description:

*Appearance.*—Herbaceous container and garden plant. Outwardly spreading to cascading growth habit. Full and bushy plants with dense foliage and inflorescences held above and beyond the foliage on wiry peduncles. Vigorous.

*Plant height.*—About 25 cm.

*Plant spread.*—About 50 cm to 60 cm.

*Lateral branches.*—Quantity: Freely branching, about ten lateral branches per plant. Length: About 40 cm. Diameter: About 3 mm. Internode length: About 2 cm to 3 cm. Texture: Smooth, glabrous. Color: 147C.

*Foliage description.*—Arrangement: Opposite, simple. Length: About 1.8 cm to 2 cm. Width: About 1.5 cm. Shape: Bipinnate; pinnatisect. Apex: Apiculate. Base: Acute. Margin: Slightly serrate. Texture, upper and lower surfaces: Slightly pubescent. Petiole length: About 5 mm. Petiole diameter: About 1 mm. Petiole texture, upper and lower surfaces: Smooth, glabrous. Color: Developing foliage, upper surface: 138A. Developing foliage, lower surface: 138B. Fully expanded foliage, upper surface: 137A; venation, 137A. Fully expanded foliage, lower surface: 138B to 138C; venation, 137A. Petiole, upper and lower surfaces: 138B.

Inflorescence description:

*Appearance.*—Daisy-type composite inflorescence form; actinomorphic. Disc and ray florets develop acropetally on a capitulum. Inflorescences displayed above and beyond the foliage on wiry peduncles; peduncles arising from upper leaf axils. Continuously and freely flowering; about 12 to 17 inflorescences and inflorescence buds per lateral stem. Inflorescences last about one week on the plant; inflorescences persistent.

*Flowering response.*—Plants flower continuously from early spring to the autumn in Germany.

*Fragrance.*—Faint.

*Inflorescence bud.*—Length: About 3 mm to 5 mm. Diameter: About 3 mm. Shape: Ovoid. Color: 151A.

*Inflorescence size.*—Diameter: About 4.5 cm to 5 cm. Depth (height): About 4.5 mm. Diameter of disc: About 8 mm.

*Ray florets.*—Length: About 2.2 cm. to 2.7 cm. Width: About 1.3 cm to 1.5 cm. Shape: Ovate. Apex: Obtuse or retuse. Base: Acute. Margin: Entire. Texture, upper and lower surfaces: Smooth, glabrous; satiny. Number of ray florets per inflorescence: About seven to eight in a single whorl. Color: When opening, upper and lower surfaces: 12A. Fully opened, upper and lower surfaces: 12A.

*Disc florets.*—Shape: Tubular; fluted at apex. Number of disc florets per inflorescence: About 50. Length: About 7 mm. Diameter: About 1 mm. Color: Immature: 146D. Mature: Close to 17C; towards the base, close to 145C.

*Phyllaries.*—Quantity: About eight to ten in a single whorl. Length: About 1.5 mm to 2 mm. Width: About 5 mm. Shape: Lanceolate. Apex: Acute. Base: Truncate. Margin: Entire. Texture, upper and lower surfaces: Smooth, glabrous. Color, immature, upper and lower surfaces: 138A. Color, mature, upper surface: 138A. Color, mature, lower surface: 137C.

*Peduncles.*—Length: About 7 cm to 10 cm. Diameter: About 1 mm. Aspect: Flexible, wiry, strong; inflorescences held above and beyond foliage. Orientation: About 35° to 45° to the stem. Texture: Smooth, glabrous. Color: 137A.

*Reproductive organs.*—Androecium: Present on disc florets only. Stamen quantity: Five per disc floret. Anther shape: Oblong. Anther length: Less than 0.5 mm. Anther color: 17B. Pollen amount: Moderate. Pollen color: 17B. Gynoecium: Present on ray and disc florets. Pistil length: About 2 mm. Style length: About 1 mm. Style color: 17B. Stigma shape: Two-parted. Stigma color: 17B. Seeds: Length: About 3 mm to 5 mm. Diameter: About 1 mm. Color: 202A.

Disease/pest resistance: Resistance to pathogens and pests common to *Bidens* has not been observed on plants of the new *Bidens*.

Temperature tolerance: Plants of the new *Bidens* have been observed to tolerate temperatures from about 0° C. to 40° C.

It is claimed:

1. A new and distinct cultivar of *Bidens* plant named 'Sumbid 03', as illustrated and described.

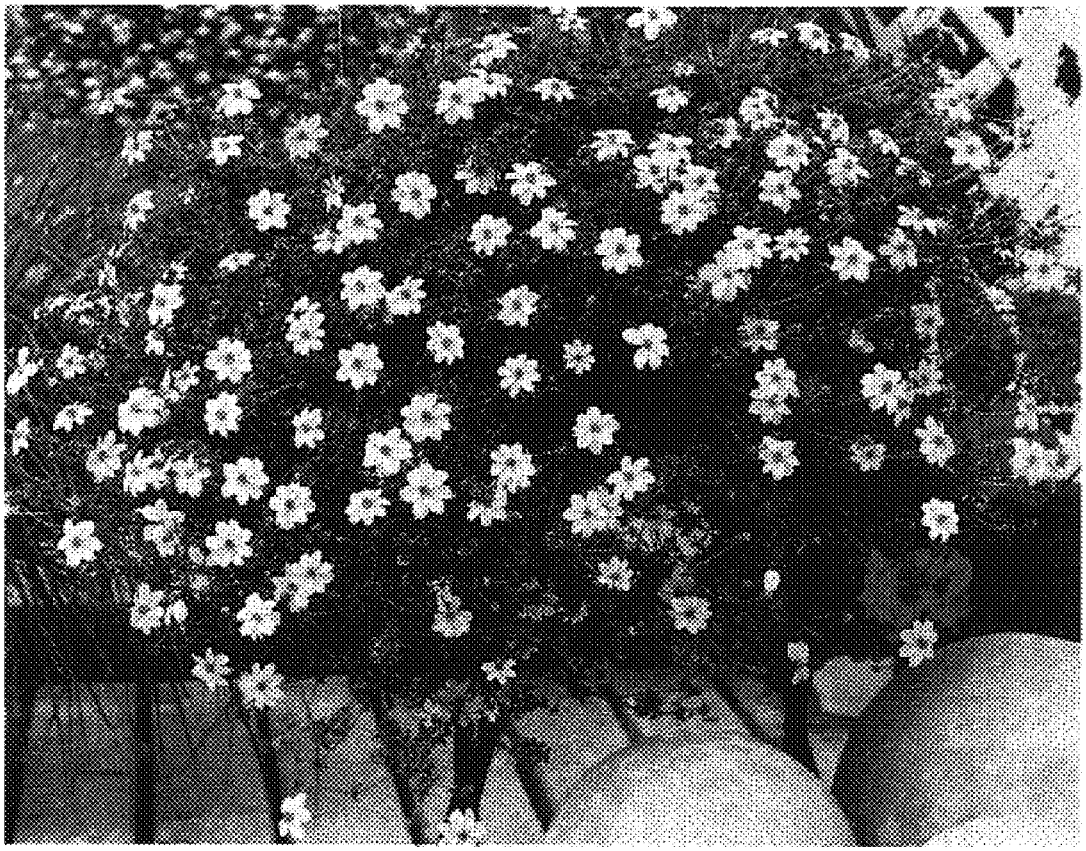

* * * * *